US00PP24068P2

(12) United States Plant Patent
de Jong

(10) Patent No.: US PP24,068 P2
(45) Date of Patent: Dec. 3, 2013

(54) ***ASTRANTIA* PLANT NAMED 'STAR OF PASSION'**

(50) Latin Name: ***Astrantia* spp. hybrid**
Varietal Denomination: Star of Passion

(76) Inventor: Jacobus Robertus de Jong, Noordwijkerhout (NL)

( * ) Notice: Subject to any disclaimer, the term of this patent is extended or adjusted under 35 U.S.C. 154(b) by 94 days.

(21) Appl. No.: 13/506,294

(22) Filed: Apr. 9, 2012

(51) Int. Cl.
*A01H 5/00* (2006.01)

(52) U.S. Cl.
USPC ..... Plt./408; Plt./263.1

(58) Field of Classification Search
USPC ..... Plt./263.1, 408
See application file for complete search history.

*Primary Examiner* — Susan McCormick Ewoldt
(74) *Attorney, Agent, or Firm* — Penny J. Aguirre

(57) ABSTRACT

A new cultivar of *Astrantia* 'Star of Passion' characterized by its flowers that are grey-white in color and dark purple tips, its flower bracts that are dark purple on the lower surface and providing high color contrast to the inflorescences, and its relatively low and compact plant habit.

2 Drawing Sheets

Botanical classification: *Astrantia* spp. hybrid.
Variety denomination: 'Star of Passion'.

RELATED APPLICATION

This application is co-pending with a U.S. Plant Patent applications filed for a cultivar derived from the same breeding program entitled *Astrantia* Plant Named 'Star of Treasure' (U.S. Plant application Ser. No. 13/506,293).

BACKGROUND OF THE INVENTION

The present invention relates to a new and distinct cultivar of *Astrantia*, botanically of hybrid origin and known as *Astrantia* 'Star of Passion' and will be referred to hereinafter by its cultivar name, 'Star of Passion'.

The new cultivar originated from open pollination done by the Inventor in 1999 in Woubrugge, The Netherlands. Both the male and female parents were unnamed plants from the Inventor's breeding program. The specific parents are not known as seeds from various female plants were pooled. The Inventor selected 'Star of Passion' as a single unique plant in 2010.

Asexual reproduction of the new cultivar was first accomplished by division by the Inventor in Woubrugge, The Netherlands in 2010. Propagation by division and tissue culture has determined that the characteristics of this cultivar are stable and are reproduced true to type in successive generations.

SUMMARY OF THE INVENTION

The following traits have been repeatedly observed and are determined to be the characteristics of 'Star of Passion'. These characteristics in combination distinguish 'Star of Passion' as a new and distinct cultivar of *Astrantia*.

1. 'Star of Passion' exhibits flowers that are grey-white in color and dark purple tips.
2. 'Star of Passion' exhibits flower bracts that are dark purple on the lower surface; providing high color contrast to the inflorescences.

3. 'Star of Passion' exhibits a relatively low and compact plant habit; reaching about 60 cm in height.

'Star of Passion' can be most closely compared to the cultivars 'Buckland' (not patented), 'Star of Beauty' (not patented) and 'Star of Treasure'. 'Buckland' differs from 'Star of Passion' in being taller in height and in having pinkish-white flowers with a tint of green and pale pink bracts. 'Star of Beauty' differs from 'Star of Passion' in having white flowers that have more purple coloration and in having bracts that are rosy purple on both surfaces. 'Star of Treasure' differs from 'Star of Passion' in having flowers that are lilac white with pink red tips and dark pink-red bracts.

BRIEF DESCRIPTION OF THE DRAWING

The accompanying colored photographs illustrate the overall appearance and distinct characteristics of a two-year old plant of the new *Astrantia* as field grown in de Hoef, The Netherlands (containerized for the photo).

The photograph in FIG. 1 provides a view of a typical flowering plant of 'Star of Passion'.

Figure 1:
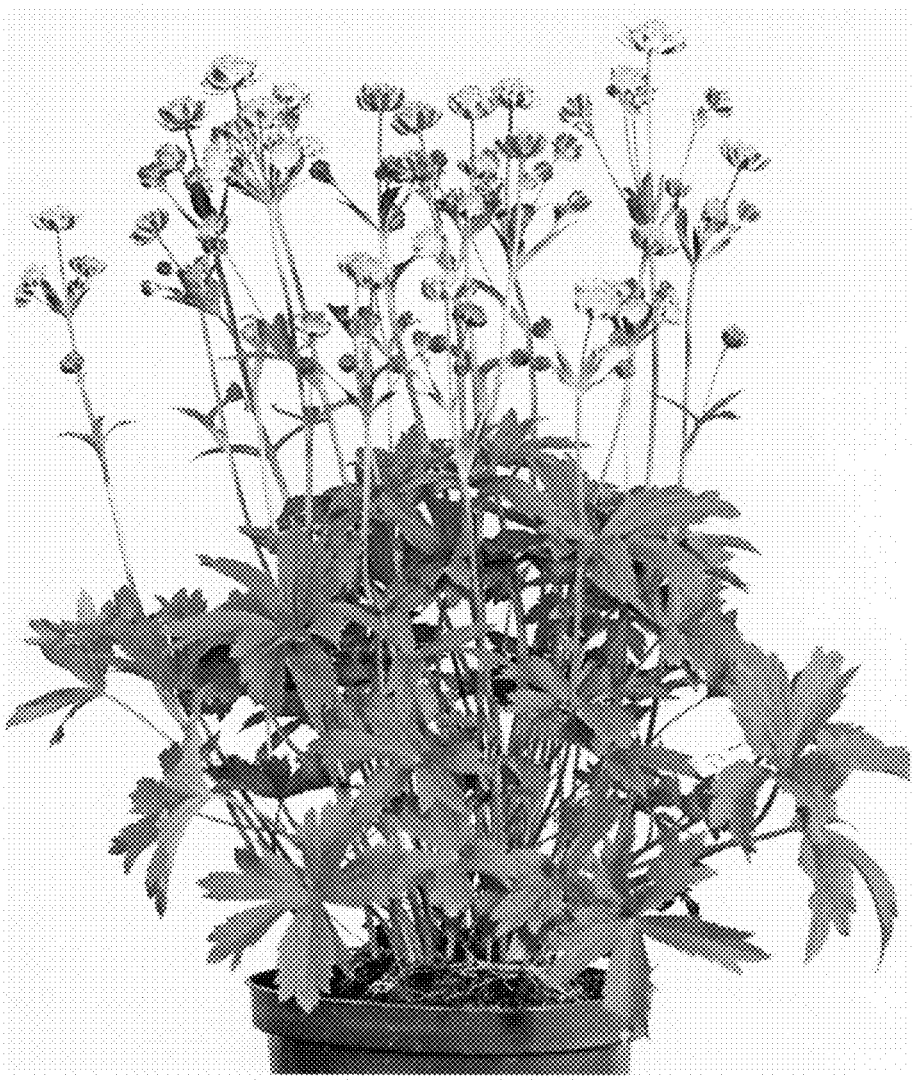
Figure 2:
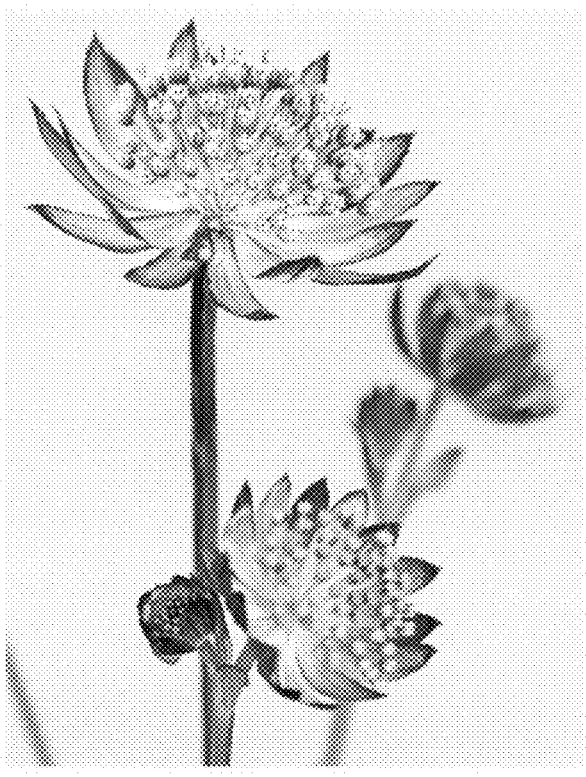

The photograph in FIG. 2 provides a close-up of the flowers 'Star of Passion'.

Figure 3:
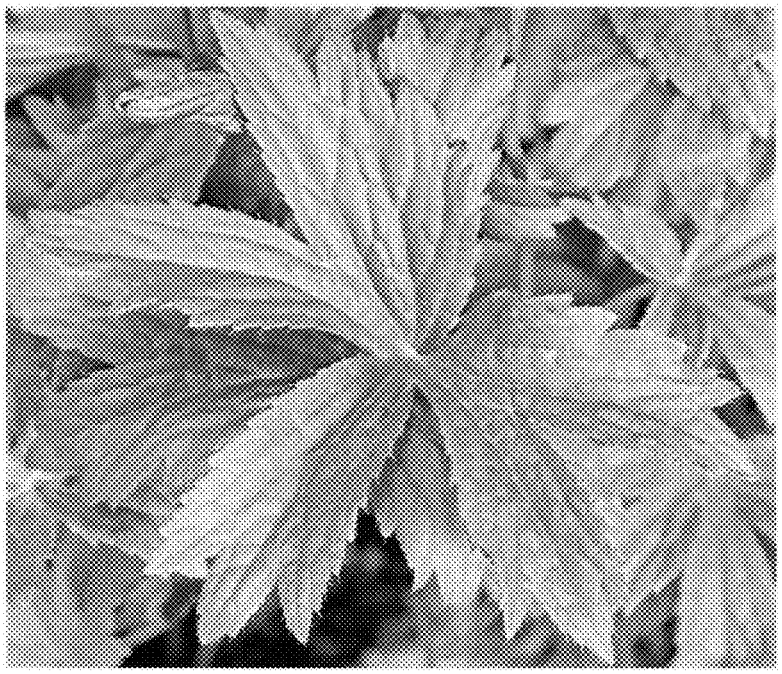

The photograph in FIG. 3 provides a close-up of a leaf 'Star of Passion'.

The colors in the photographs are as close as possible with the photographic and printing technology utilized. The color values cited in the detailed botanical description accurately describe the colors of the new *Astrantia*.

DETAILED BOTANICAL DESCRIPTION

The following is a detailed description of two-year-old plants of the new cultivar as field grown outdoors in De Hoef, Netherlands. Plants were grown under average day temperatures ranging from 15° to 28° C. and average night temperatures of 5° to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Herbaceous perennial.

*Blooming period.*—June to mid August in The Netherlands.

*Plant habit.*—Basal rosette with flowering stems growing from the base, ovate to broad oblong in shape.

*Height and spread.*—Reaches about 60 cm in height and 52.5 cm in diameter.

*Hardiness.*—Cold hardy at least to U.S.D.A Zone 6 and Heat tolerant at least to 30° C.

*Disease resistance.*—Not more susceptible to pests and diseases than other *Astrantia*.

*Root description.*—Dense, fine, freely branched.

*Propagation.*—Tissue culture or division.

*Growth rate.*—Moderate.

Stem description:

*Stem shape.*—Round.

*Stem color.*—Base and center 144A, blending vertically upward to apex and becoming 148A, heavily tinged N199A.

*Stem size.*—Average of 40.1 cm in length (excluding inflorescence) and 4 mm in diameter.

*Stem surface.*—Slightly glossy, ribbed vertically.

*Stem strength.*—Strong.

*Branching habit.*—Stems grow freely from basal rosette, about 19 flowering stems.

Foliage description:

*Leaf division.*—Simple.

*Leaf shape.*—Palmately parted.

*Leaf base.*—Hastate, basal lobes of each leaf slightly overlapping.

*Leaf apex.*—Acute.

*Leaf margin.*—Biserrate, teeth aristate.

*Leaf venation.*—Laciniate in pattern, upper veins; 143B, lower veins; 144B.

*Leaf attachment.*—Petiolate.

*Leaf arrangement.*—Basal rosette, one stem per leaf per stem is present.

*Leaf surface.*—Upper and lower surface; smooth and slightly glossy.

*Leaf color.*—Young upper surface 143A, base 143B to 144A, young lower surface 143B, mature upper surface; a color between N137B to 137C, lower surface 146B.

*Leaf size.*—Basal leaves average 10.5 cm in length and 13.9 cm in width, stem leaves average 9.2 cm in length and 10.9 cm in width.

*Leaf number.*—Sheathing, average of 57 leaves per plant, average of 38 are in the basal rosette.

*Petiole.*—Basal leaves; average 22 cm in length, 4 mm in diameter, 3 mm in width, ovate in shape, 144B in color, stem leaf; winged (sheathed), average of 5.8 cm in length, 3.7 cm in height and 3 mm in width.

Flower description:

*Inflorescence type.*—Compound umbel of numerous campanulate flowers subtended by showy involucral bracts.

*Lastingness of inflorescence.*—Average of 12 days, self cleaning.

*Inflorescence size.*—Terminal; average of 14.7 cm in height (including peduncle) and 10.7 cm in width, umbel; average of 2.7 cm in height and 4.2 cm in width.

*Inflorescence fragrance.*—Moderate, sweet, pleasant.

*Flower number.*—Average of 80 per umbel, average of 8 umbels per compound umbel, average of 640 flowers per flowering stem.

*Flower form.*—Umbel (compound).

*Flower aspect.*—Upright and upright-outward.

*Flower bud size.*—Average of 2 mm in length, average of 1.75 mm in diameter.

*Flower bud color.*—138A, apex 155A.

*Flower bud shape.*—Obovate with flattened apex.

*Flower size.*—Average of 4 mm in diameter and 1 cm in height.

*Corolla features.*—Petals are un-fused and upright.

*Petal number.*—5.

*Petal shape.*—Narrow ovate, incurved.

*Petal color.*—Opening and fully open upper and lower surfaces; 155A.

*Petal surface.*—Dull, smooth.

*Petal margins.*—Entire.

*Petal apex.*—Narrowly acute.

*Petal size.*—Average of 2 mm in length and 1 mm in width.

*Calyx form.*—Rotate, held upright.

*Calyx size.*—Average of 2 mm in length and 2 mm in diameter.

*Sepal number.*—5.

*Sepal shape.*—Narrow ovate.

*Sepal margin.*—Entire.

*Sepal size.*—Average of 2 mm length, 0.6 mm in width (at base).

*Sepal surface.*—Dull, smooth.

*Sepal apex.*—Broadly acute.

*Sepal base.*—Cuneate.

*Sepal color.*—Young and mature upper and lower surfaces; 137B, margins and apex; 157A to 157D.

*Peduncle size.*—Average of 15.7 cm in length and 2.5 mm in diameter.

*Peduncle strength/aspect.*—Strong, terminals held upright, secondary held at an average of 35° from stem.

*Peduncle color.*—148A, heavily tinged N199A.

*Pedicel size.*—Average of 7 mm in length and 0.3 mm in width.

*Pedicel strength/aspect.*—Strong, terminal held upright, secondary held at 80° from stem.

*Pedicel color.*—157D.

*Inflorescent leaves.*—About 3 per inflorescence, sessile, about 2.5 cm in length and 3.5 cm in width, palmately lobed with acute apex, entire margin and cuneate base, color between N137B to 137C on upper surface and 146B on lower surface, both surfaces are can be tinged with N186D.

Involucral bracts:

*Bract number.*—About 20.

*Bract shape.*—Elliptic to narrow obovate.

*Bract size.*—About 2.1 cm in depth and 5 mm in width.

*Bract color.*—Upper surface; between 195B and N195C, margins; 187A to 187B, lower surface upper row; between 157C and 157D, base and tip; between N186A and 187A, main veins; 144B, lower surface lower row; N186D with darker tip and main vein; N186C.

*Bract texture.*—Dull and smooth.

*Bract apex.*—Acute, with two small teeth near the top.

*Bract base.*—Attenuate

*Bract margins.*—Entire. .

Reproductive organs:

*Gynoecium.*—2 pistils, about 3.5 mm in length, stigma is club-shaped and 187A in color, style is about 3.3 mm in length, N186B to 186D in color, becoming lighter towards base, ovary is 193A in color.

*Androcoecium.*—5 stamens, anthers are dorsifixed, elliptic in shape, about 0.5 mm in length and 187A in color, filament is about 4 mm in length and 155A in color, pollen is low in abundance and 156D in color.

*Fruit/seeds.*—No fruit set (or seeds) have been observed to date.

It is claimed:

1. A new and distinct cultivar of *Astrantia* plant named 'Star of Passion' as herein illustrated and described.

* * * * *